(12) United States Patent     (10) Patent No.:   US 12,602,879 B2

You                 (45) Date of Patent:     Apr. 14, 2026

---

(54) METHOD AND DEVICE FOR PROVIDING SURGICAL GUIDE USING AUGMENTED REALITY

(71) Applicant: KOREA UNIVERSITY RESEARCH AND BUSINESS FOUNDATION, Seoul (KR)

(72) Inventor: Hijin You, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 461 days.

(21) Appl. No.: 17/916,043

(22) PCT Filed: Feb. 23, 2021

(86) PCT No.: PCT/KR2021/002234

§ 371 (c)(1),
(2) Date: Mar. 16, 2023

(87) PCT Pub. No.: WO2021/201434

PCT Pub. Date: Oct. 7, 2021

(65) Prior Publication Data

US 2024/0104853 A1     Mar. 28, 2024

(30) Foreign Application Priority Data

Apr. 1, 2020    (KR) ........................ 10-2020-0039897

(51) Int. Cl.
    *G06T 19/00*       (2011.01)
    *A61B 34/10*       (2016.01)
    (Continued)

(52) U.S. Cl.
    CPC ............ *G06T 19/006* (2013.01); *A61B 34/10* (2016.02); *A61B 90/361* (2016.02); *A61B 90/39* (2016.02);
    (Continued)

(58) Field of Classification Search
None
See application file for complete search history.

(56) References Cited

U.S. PATENT DOCUMENTS

| | | | |
|---|---|---|---|
| 10,485,614 B2 | 11/2019 | Jang | |
| 2017/0367766 A1* | 12/2017 | Mahfouz | .............. A61B 8/4472 |

(Continued)

FOREIGN PATENT DOCUMENTS

| | | |
|---|---|---|
| JP | 2018511359 | 4/2018 |
| JP | 2020506745 | 3/2020 |

(Continued)

OTHER PUBLICATIONS

Ritto et al. (Comparison of the accuracy of maxillary position between conventional model surgery and virtual surgical planning, Oral & Maxillofacial surgery, 2018) (Year: 2018).*

*Primary Examiner* — Kyle Zhai

(74) *Attorney, Agent, or Firm* — JCIPRNET

(57) ABSTRACT

A method and device for a surgical guide using augmented reality (AR) is disclosed. The surgical guide method using AR includes obtaining an image showing a surgery subject by using a camera of a wearable device worn by a user, recognizing a marker predefined in the image, determining expression attribute information of a three-dimensional (3D) image model to be projected onto the surgery subject based on the recognized marker, and displaying the 3D image model through the wearable device by projecting the 3D image model onto the surgery subject, based on the determined expression attribute information.

13 Claims, 8 Drawing Sheets

(51) Int. Cl.
    *A61B 90/00*         (2016.01)
    *G06F 3/01*          (2006.01)
    *G06T 19/20*        (2011.01)

(52) U.S. Cl.
    CPC ............. *G06F 3/017* (2013.01); *G06T 19/20*
         (2013.01); *A61B 2090/365* (2016.02); *A61B*
           *2090/366* (2016.02); *G06T 2219/2016*
                              (2013.01)

(56)                References Cited

U.S. PATENT DOCUMENTS

| | | | |
|---|---|---|---|
| 2018/0022031 A1* | 1/2018 | Ishii ...................... | B29C 64/386 |
| | | | 156/235 |
| 2018/0096537 A1* | 4/2018 | Kornilov ............... | G06V 20/20 |
| 2019/0012944 A1* | 1/2019 | Hall ....................... | A61B 34/25 |
| 2020/0188028 A1* | 6/2020 | Feiner ................... | G16H 50/50 |
| 2021/0059760 A1* | 3/2021 | Tseng ..................... | G06T 19/20 |
| 2021/0346091 A1* | 11/2021 | Haslam ................. | G16H 30/40 |

FOREIGN PATENT DOCUMENTS

| | | |
|---|---|---|
| KR | 1020140112207 | 9/2014 |
| KR | 1020170111707 | 10/2017 |
| KR | 101843992 | 5/2018 |
| KR | 101988531 | 9/2019 |
| KR | 102056930 | 12/2019 |
| KR | 1020200026851 | 3/2020 |

* cited by examiner

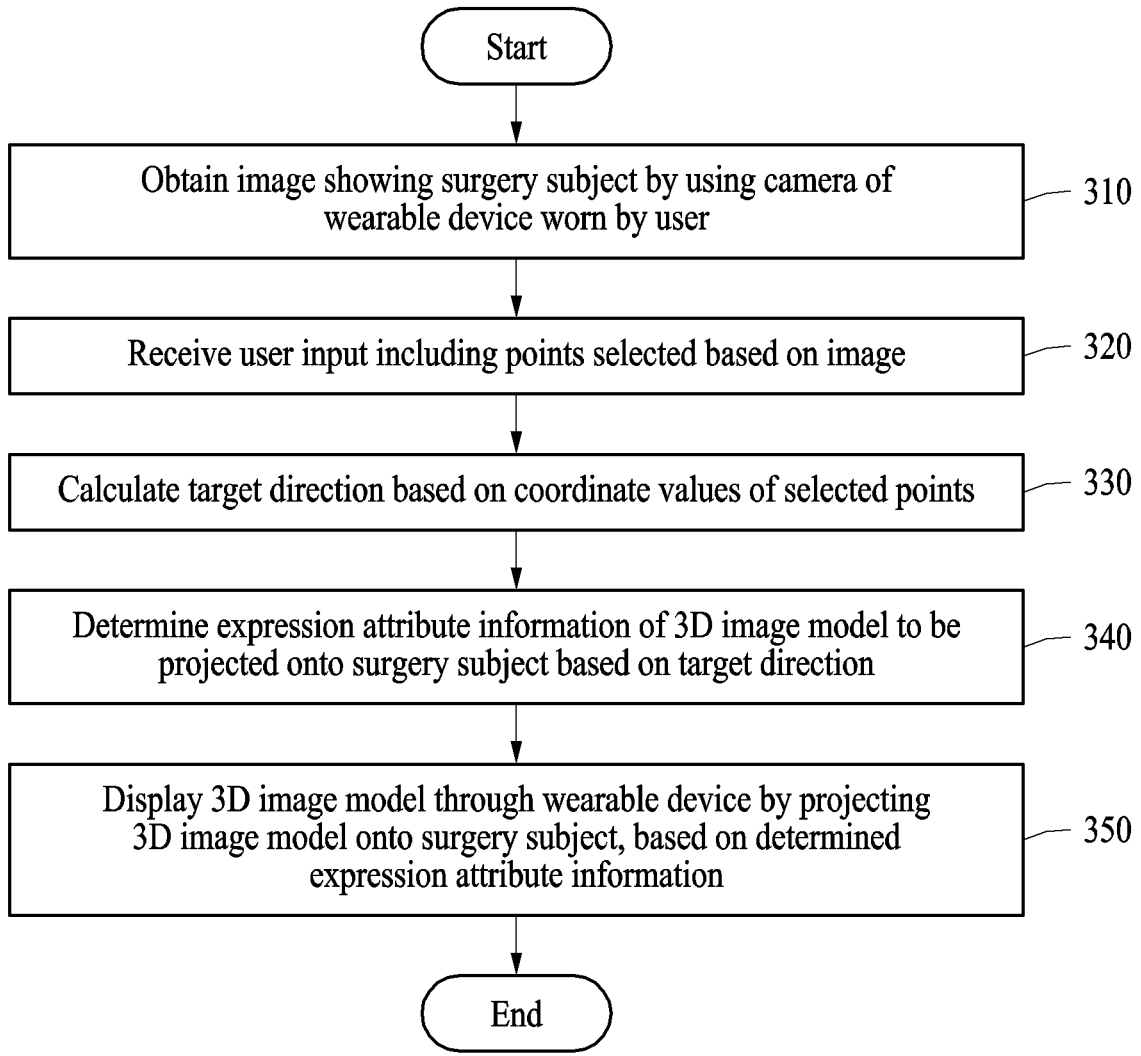

Start

Obtain image showing surgery subject by using camera of wearable device worn by user — 310

Receive user input including points selected based on image — 320

Calculate target direction based on coordinate values of selected points — 330

Determine expression attribute information of 3D image model to be projected onto surgery subject based on target direction — 340

Display 3D image model through wearable device by projecting 3D image model onto surgery subject, based on determined expression attribute information — 350

End

FIG. 3

METHOD AND DEVICE FOR PROVIDING SURGICAL GUIDE USING AUGMENTED REALITY

TECHNICAL FIELD

The following description relates to a surgical guide method using augmented reality (AR) and a surgical guide device for performing the surgical guide method using the AR.

BACKGROUND ART

Augmented reality (AR) is a technology for overlaying a virtual world having additional information in real time on the real world to show them in a single image. The AR technology is usefully applicable particularly to assist surgery in the medical field, because the technology provides visible information. The AR technology may provide image information necessary for surgeries, provide a simulation of a surgery to surgeons in a pre-operative planning stage, and function as a navigation system during the surgery. The AR system for bone tumor surgery developed in the related art has been applied to actual surgery. In this case, a location of the tumor obtained from an imaging study is implemented in the AR on a patient's surgical field, to exhibit an effect of increasing surgical precision while minimizing a resection range.

In order to use the AR technology in an operating room practically, a surgeon needs to be able to see necessary information in front of his or her eyes with both hands aseptically free. It is expected that wearable devices, such as Google Glass or Microsoft HoloLens, play an important role in transferring AR images, and related studies are being actively conducted. A European company has developed a holographic navigation platform for spine surgeries. The holographic navigation platform for spinal surgeries may show a site, that a surgeon is not able to see as an AR-based graphic by using the wearable AR devices. Through this, it is demonstrated that the holographic navigation platform for spine surgeries has the potential to improve the precision and speed of surgeries.

Although the application of the AR technology in the medical field is emerging as a future medical technology, the AR technology of the related art has limitations in being applied to clinical practice requiring precision. In order for the AR technology to be universally applied to clinical practice, research on a method of improving tracking accuracy, accurately recognizing augmented information, and naturally interacting with the augmented information is required.

DISCLOSURE OF THE INVENTION

Technical Solutions

A surgical guide method using augmented reality (AR) according to an example embodiment may include obtaining an image showing a surgery subject by using a camera of a wearable device worn by a user, recognizing a marker predefined in the image, determining expression attribute information of a three-dimensional (3D) image model to be projected onto the surgery subject based on the recognized marker, and displaying the 3D image model through the wearable device by projecting the 3D image model onto the surgery subject, based on the determined expression attribute information.

The recognizing of the marker may include recognizing at least one of position information of the marker, size information of the marker, or shape information of the marker based on the image.

The determining of the expression attribute information of the 3D image model may include determining at least one of position information, shape information, or rotation information of the recognized marker based on the predefined marker, and determining the expression attribute information of the 3D image model to be projected onto the surgery subject based on at least one of the determined position information, shape information, or rotation information.

The determining of the expression attribute information of the 3D image model may include determining at least one of direction information, size information, or position information of the 3D image model to be projected onto the surgery subject.

The surgical guide method according to an example embodiment may further include, when an input of a user's gesture is detected, determining expression attribute information of the 3D image model based on the gesture.

A medical image corresponding to the surgery subject may be converted based on a horizontal plane and the 3D image model may be generated based on the converted medical image.

A surgical guide method using AR, the surgical guide method may include obtaining an image showing a surgery subject by using a camera of a wearable device worn by a user, receiving a user input including points selected based on the image, calculating a target direction based on coordinate values of the selected points, determining expression attribute information of a 3D image model to be projected onto the surgery subject based on the target direction, and displaying the 3D image model through the wearable device by projecting the 3D image model onto the surgery subject, based on the determined expression attribute information.

The target direction may be a direction perpendicular to a horizontal plane including the selected points.

The determining of the expression attribute information of the 3D image information may include determining a Z-axis direction of the 3D image model based on a straight line connecting reference points previously set in the 3D image model and a straight line connecting the selected points.

A medical image corresponding to the surgery subject may be converted based on a horizontal plane and the 3D image model may be generated based on the converted medical image.

The surgical guide method according to an example embodiment may further include, when an input of a user's gesture is detected, determining expression attribute information of the 3D image model based on the gesture.

A surgical guide device for performing a surgical guide method using AR according to an example embodiment, the surgical guide device may include an image obtainer configured to obtain an image showing a surgery subject by using a camera of a wearable device worn by a user, a recognizer configured to recognize a marker predefined in the image, an attribute information determiner configured to determine expression attribute information of a 3D image model to be projected onto the surgery subject based on the recognized marker, and a display configured to display the 3D image model through the wearable device by projecting the 3D image model onto the surgery subject, based on the determined expression attribute information.

The recognizer may recognize at least one of position information of the marker, size information of the marker, or shape information of the marker based on the image.

The attribute information determiner may determine at least one of position information, shape information, or rotation information of the recognized marker based on the predefined marker, and determine the expression attribute information of the 3D image model to be projected onto the surgery subject based on at least one of the determined position information, shape information, or rotation information.

The attribute information determiner may determine at least one of direction information, size information, or position information of the 3D image model to be projected onto the surgery subject.

When the recognizer detects an input of a user's gesture, the attribute information determiner may determine the expression attribute information of the 3D image model based on the gesture.

A medical image corresponding to the surgery subject may be converted based on a horizontal plane and the 3D image model may be generated based on the converted medical image.

A surgical guide device for performing a surgical guide method using AR according to another example embodiment, the surgical guide device may include an image obtainer configured to obtain an image showing a surgery subject by using a camera of a wearable device worn by a user, a recognizer configured to receive a user input including points selected based on the image, an attribute information determiner configured to calculate a target direction based on coordinate values of the selected points and determine expression attribute information of a 3D image model to be projected onto the surgery subject based on the target direction, and a display configured to display the 3D image model through the wearable device by projecting the 3D image model onto the surgery subject, based on the determined expression attribute information.

The target direction may be a direction perpendicular to a plane including the selected points.

The attribute information determiner may determine a Z-axis direction of the 3D image model based on a straight line connecting reference points previously set in the 3D image model and a straight line connecting the selected points.

When the recognizer detects an input of a user's gesture, the attribute information determiner may determine expression attribute information of the 3D image model based on the gesture.

Effects

According to an example embodiment, through the wearable device worn by the operator, an operator may be provided with, during an operation, an image, in which a medical picture, an anatomical structure, or an image obtained from imaging examination of a patient, which is implemented three-dimensionally, is superimposed on a surgical site of the surgery subject, based on an augmented reality technology.

According to an example embodiment, the operator may check an image captured before the operation without looking away from or leaving an operating table to check a monitor, and efficiency and precision of the operation may be enhanced since the operator may check a computed tomography (CT) image projected onto a patient's face.

According to an example embodiment, the operator may check a three-dimensional (3D) structure, which is difficult to understand with a two-dimensional screen, as a 3D hologram in front of his or her eyes, while adjusting a direction, size, and position thereof to a desired direction, size, and position through a gesture control function.

According to an example embodiment, a medical picture, an anatomical structure, or an image obtained from imaging examination of a patient, which is implemented three-dimensionally, may be accurately projected onto the surgical site.

According to an example embodiment, a medical picture, an anatomical structure, or an image obtained from imaging examination of a patient, which is implemented three-dimensionally, may be projected onto an accurate position by tracking and learning a space more accurately using markers positioned on a horizontal plane.

BRIEF DESCRIPTION OF DRAWINGS

FIG. 3 is a flowchart illustrating a surgical guide method according to another example embodiment.

BEST MODE FOR CARRYING OUT THE INVENTION

Figure 1:
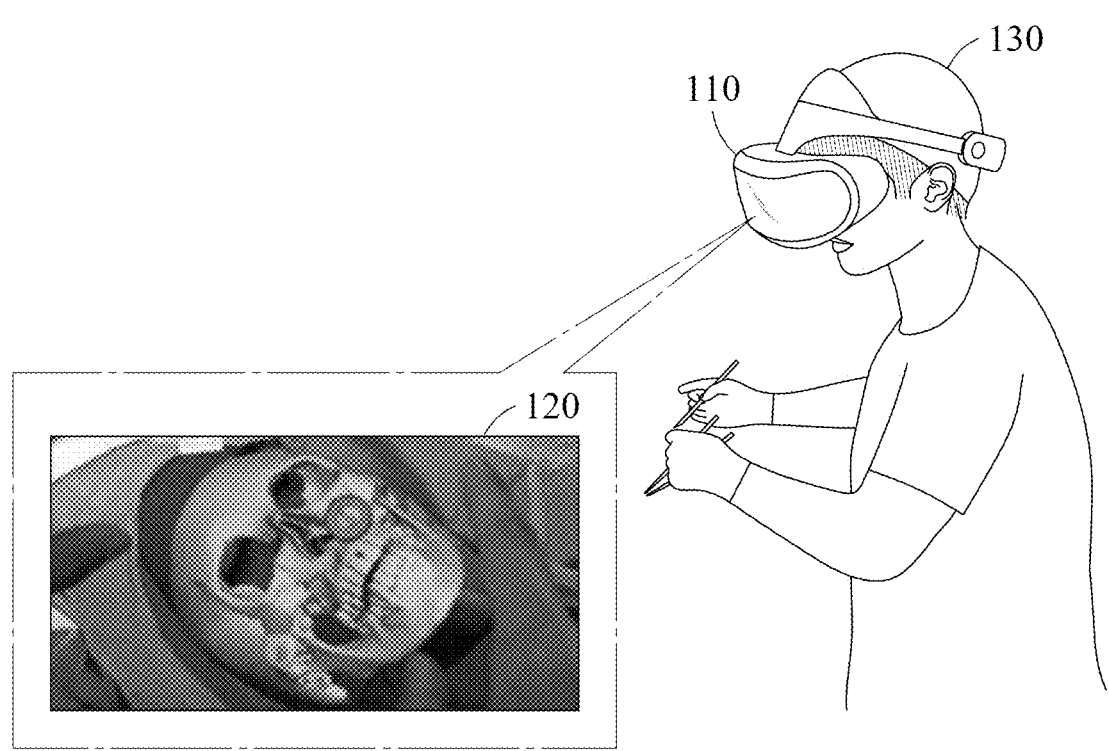
FIG. 1 is a diagram schematically illustrating a surgical guide method using augmented reality (AR) according to an example embodiment.

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like components and a repeated description related thereto will be omitted. In the description of example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the example embodiments. These terms are used only for the purpose of discriminating one component from another component, and the nature, the sequences, or the orders of the components are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

FIG. 1 is a diagram schematically illustrating a surgical guide method using augmented reality (AR) according to an example embodiment.

The surgical guide method using AR may relate to the construction of a surgical platform using an AR technology. The surgical guide method of the present disclosure may be described based on the construction of a plastic surgery platform, but the surgical guide method is not limited to the field of plastic surgery and may be applied to other fields. The surgical guide method may provide a surgical guide or navigation function for converting image data (a clinical photograph, a computed tomography (CT) image, etc.) of a patient into a three-dimensional (3D) hologram and matching the 3D hologram to an affected part by using a wearable device. The surgical guide method of the present disclosure may provide, through a face of a surgery subject, a method of matching and tracking a feature point that is a core of the AR-based technology. Particularly, the surgical guide method of the present disclosure may be provided through the zygomatic fracture of the face. However, the surgical guide method described in the present disclosure is not limited to the face and may be performed on other body parts.

A surgical guide device for performing the surgical guide method may be an AR wearable device or a separate device connected to the wearable device by wire or wirelessly. The surgical guide device may be, for example, any one of a computing device or a smart terminal connected to the wearable device. The surgical guide device may convert a medical image corresponding to a facial bone of a surgery subject into a 3D image model. The surgical guide device may generate an efficient 3D image model by reducing the number of polygons by a method of keeping only a lesion portion necessary for each patient in detail and removing other unnecessary portions or maintaining only a shape thereof such that the medical image is suitable for the wearable device to process. In addition, according to an example embodiment, the surgical guide device may adjust brightness of the medical image.

Calibration of the surgical guide method of the present disclosure may be performed in two example embodiments. The surgical guide method according to an example embodiment may perform calibration by a method of recognizing position, shape, and size of a surgery subject based on a field of view of a user through a marker having predefined position, shape, and size, and projecting a 3D image model onto the surgery subject based on the recognized information. The surgical guide method according to another example embodiment may perform calibration by matching three points on a surgical site selected by a user input to reference points on a predefined 3D image model.

Referring to FIG. 1, a user 130 wearing an AR wearable device 110 may be provided with a field of view 120 such as a 3D image model projected onto a surgery subject through the AR wearable device 110. Herein, the user 130 may be a doctor performing an operation or medical staff participating in the operation.

The surgical guide device may obtain an image showing a surgery subject by using a camera of the wearable device 110. The surgical guide device may recognize a surgery subject based on the image. The surgical guide device may determine expression attribute information of the 3D image model based on the recognized surgery subject. The surgical guide device may display the 3D image model through the wearable device 110 by projecting the 3D image model onto the surgery subject, based on the determined expression attribute information of the 3D image model.

The user 130 may input a gesture based on the field of view provided through the AR wearable device 110. The surgical guide device may display the 3D image model adjusted based on the gesture through the AR wearable device 110.

Figure 2:
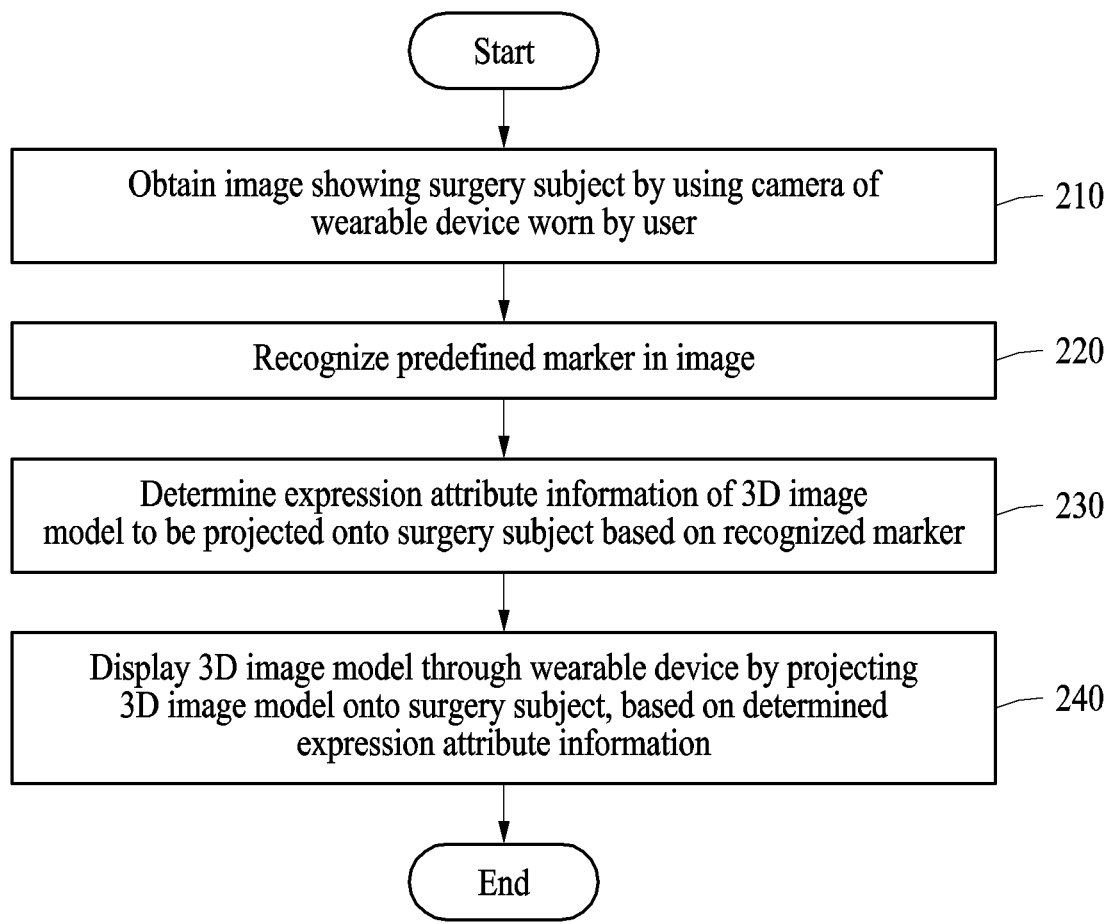
FIG. 2 is a flowchart illustrating a surgical guide method according to an example embodiment.

FIG. 2 is a flowchart illustrating a surgical guide method according to an example embodiment.

Referring to FIG. 2, in operation 210, a surgical guide device may obtain an image showing a surgery subject by using a camera of a wearable device worn by a user. Herein, the surgical guide device may be a wearable device worn by the user or a separate device connected to the wearable device by wire or wirelessly. In addition, the user may be a doctor performing an operation or medical staff participating in the operation.

In operation 220, the surgical guide device may recognize a predefined marker in the image. The size and shape of the marker may be predefined. In addition, based on a position where the marker is attached, the surgery subject may be positioned at a predetermined position. For example, the marker may be attached to a flat surface of an operating table, and the surgery subject may lie down on the operating table at a predetermined position. The marker may have a square shape with one side of 10 centimeters (cm), and may be positioned at a position based on 25 cm from a median portion of the surgery subject, 20 cm from the floor to glabella, and 10 cm from the top of the operating table to the glabella.

The surgical guide device may recognize at least one of position information of the marker, size information of the marker, or shape information of the marker based on the image.

In operation 230, the surgical guide device may determine expression attribute information of the 3D image model to be projected onto the surgery subject based on the recognized marker. In an example embodiment, the surgical guide device may determine at least one of position information, shape information, or rotation information of the recognized marker based on a predefined marker. The surgical guide device may determine the expression attribute information of the 3D image model to be projected onto the surgery subject, based on at least one of the determined position information, shape information, or rotation information. The surgical guide device may learn and track a space, in which the surgery subject is positioned, by performing comparison of at least one of position information, shape information, or rotation information between the predefined marker and the recognized marker. The surgical guide device may learn and track the space, in which the surgery subject is positioned, to determine a position, size, and rotation angle of the surgery subject in an image collected by the camera, and determine the expression attribute information of the 3D image model to be projected onto the surgery subject based on the determined result. In this case, the surgical guide device may determine the expression attribute information of the 3D image model to be projected onto the surgery subject by determining at least one of direction information, size information, or position information of the 3D image model to be projected onto the surgery subject.

In operation 240, the surgical guide device may display the 3D image model through the wearable device by projecting the 3D image model onto the surgery subject, based on the determined expression attribute information. The user may be provided with an image in which the 3D image model corresponding to a surgical site is projected onto the surgical site in an image including the surgery subject output through the wearable device. The image including the surgery subject may be provided at the same time point as the field of view of the user. The user may be provided with, through the wearable device, an image in which the 3D image model is matched to and projected onto a portion corresponding to the 3D image model. The surgical guide device may track and learn the space for each predetermined period, to determine expression attribute information of the 3D image model according to movement of the user. Accordingly, the surgical guide device may provide a surgical guide platform based on the AR technology according to the movement of the user.

In another example embodiment, when an input of a user's gesture is detected, the surgical guide device may determine the expression attribute information of the 3D image model based on the gesture. That is, the surgical guide device may adjust the expression attribute information of the 3D image model determined in operation 230 based on the user's gesture. Accordingly, the surgical guide device may provide an interaction function capable of more precisely projecting the 3D image model onto the surgery subject.

In an example embodiment, the medical image may include at least one of a CT image or an MRI image corresponding to the surgery subject. In an example embodiment, the medical image corresponding to the surgery subject may be converted to have .fbx/.obj/.mb/.ma/.max extensions from a DICOM extension and the medical image corresponding to the surgery subject may be converted based on a horizontal plane. Accordingly, the 3D image model may be generated based on the converted medical image. In addition, according to an example embodiment, the medical image may further include a 3D scan image since the 3D scan image of the surgery subject may also be directly used with the extensions of .obj and .jbx.

The software used for the conversion of the medical image may be any one of Slicer, InVesalius, 3Ds max, blender, or MeshLab. The software used for the conversion of the medical image is not limited to the software described herein. The quality of the converted model varies according to three reference planes of a horizontal plane, a coronal plane, and a sagittal plane, and the medical image is characterized in that the smallest amount of a step phenomenon occurs when the conversion is performed based on the horizontal plane. Since the DICOM extension reflects an actually measured size, a file extracted from the medical image may be converted into a 3D object as it is without a size change in 3Ds max, which is a 3D modeling program.

FIG. 3 is a flowchart illustrating a surgical guide method according to another example embodiment.

Referring to FIG. 3, in operation 310, the surgical guide device may obtain an image showing a surgery subject by using a camera of a wearable device worn by a user. The obtained image herein may have the same field of view and time point as those of the user wearing the wearable device.

In operation 320, the surgical guide device may receive a user input including points selected based on the image. The surgical guide device may display the obtained image through the wearable device. In the above example embodiment, the user may select three points based on the displayed image. Herein, the three points may indicate the two eyes and the chin. The surgical guide device may learn and track a space, in which the surgery subject is positioned, based on coordinate values of the selected points.

In operation 330, the surgical guide device may calculate a target direction based on the coordinate values of the selected points. The target direction herein may be characterized in that the target direction is a direction perpendicular to the horizontal plane including the selected points. Also, the target direction may indicate a normal vector.

In operation 340, the surgical guide device may determine the expression attribute information of the 3D image model to be projected onto the surgery subject based on the target direction. In the example embodiment, the surgical guide device may determine position information and size information of the 3D image model to face the direction perpendicular to the horizontal plane including the selected points, by utilizing the target direction of the horizontal plane including the selected points. In addition, the surgical guide device may determine the expression attribute information of the 3D image model by determining a Z-axis direction of the 3D image model based on a straight line connecting reference points previously set in the 3D image model and a straight line connecting the selected points.

In operation 350, the surgical guide device may display the 3D image model through the wearable device by projecting the 3D image model onto the surgery subject, based on the determined expression attribute information. The surgical guide device may provide the user with an image in which the 3D image model is matched to the surgery subject through the learning and tracking of the space. The user may be provided with an image as if the 3D image model is attached to the surgical site through the wearable device.

When the surgical guide device detects the input of the user's gesture, the surgical guide device may determine the expression attribute information of the 3D image model based on the gesture. The determining of the expression attribute information of the 3D image model by the surgical guide device based on the user's gesture is also applicable to this example embodiment in the same manner as in the example embodiment corresponding to FIG. 2.

As described in the detailed description of FIG. 2, the medical image corresponding to the surgery subject may be converted based on the horizontal plane and the 3D image model may be generated based on the converted medical image.

Figure 4:
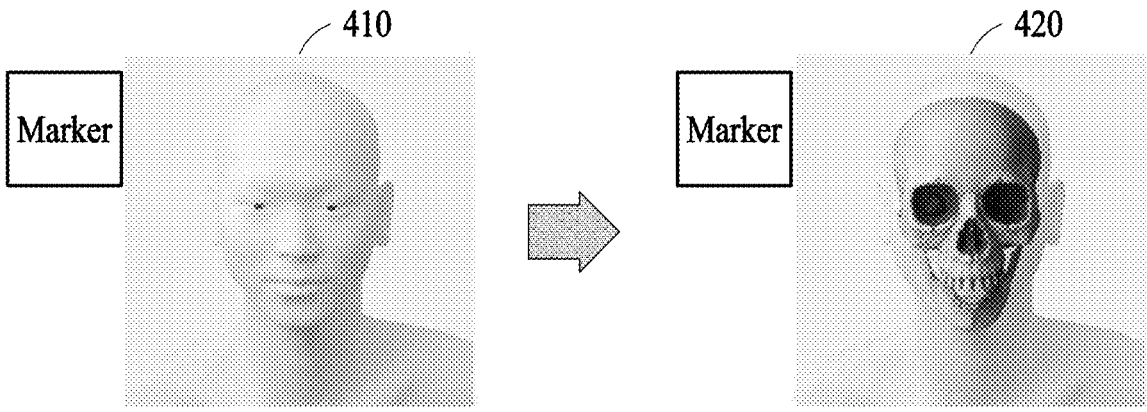
FIG. 4 is a diagram illustrating a method of projecting a three-dimensional (3D) image model onto a surgery subject according to an example embodiment.

FIG. 4 is a diagram illustrating a method of projecting a 3D image model onto a surgery subject according to an example embodiment.

Referring to FIG. 4, in operation 410, the surgical guide device may recognize a marker. The marker may have predefined absolute size, shape, and position information. The surgical guide device may compare a relative size, shape, and position of the recognized marker with the predefined absolute size, shape, and position of the marker. In this case, it may be assumed that the surgery subject is positioned at a predetermined position based on the position of the marker. For example, the marker may be attached to a corner of the operating table, and the surgery subject may lie down on the operating table at a predetermined position with respect to the marker. The marker may have a square shape with one side of 10 cm, and may be positioned at a position based on 25 cm from a median portion of the surgery subject, 20 cm from the floor to glabella, and 10 cm from the top of the operating table to the glabella.

The surgical guide device may calculate a size, position, and rotation angle of the surgery subject from the image obtained through the wearable device, based on the absolute information of the predefined marker and the relative information of the recognized marker. The surgical guide device may determine expression attribute information including at least one piece of information such as a rotation angle, size, or position of the 3D image model to be projected onto the surgery subject based on the size, position, and rotation angle of the surgery subject in the image. In operation 420, the surgical guide device may project the 3D image model onto the surgery subject, based on the determined expression attribute information of the 3D image model. A user wearing the wearable device may be provided with an image, in which the 3D image model is projected onto the surgery subject. The surgical guide device may provide an image as if the 3D image model is attached to the surgery subject.

Figure 5A:
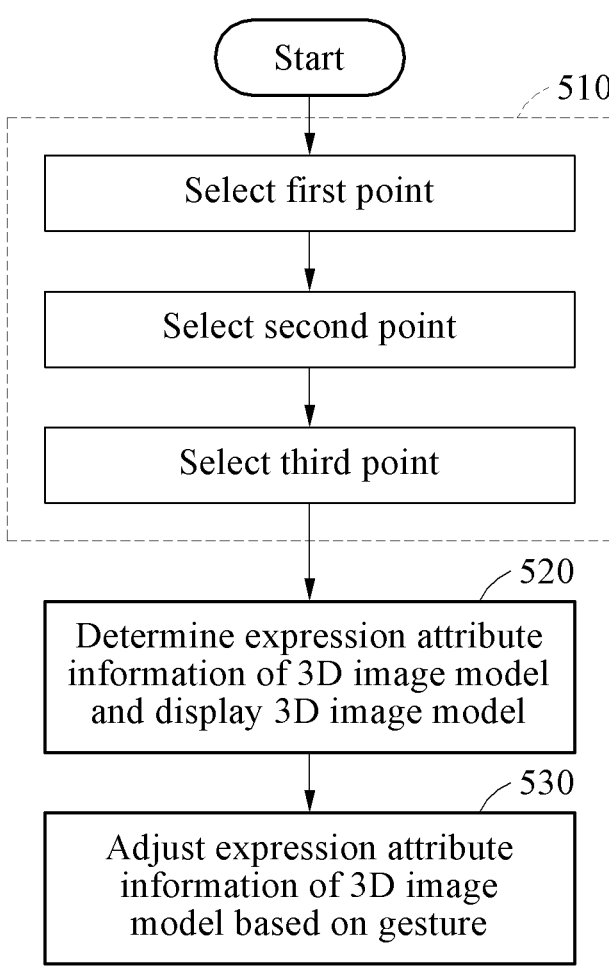
FIGS. 5A and 5B are diagrams illustrating a method of projecting a 3D image model onto a surgery subject according to another example embodiment.
Figure 5B:
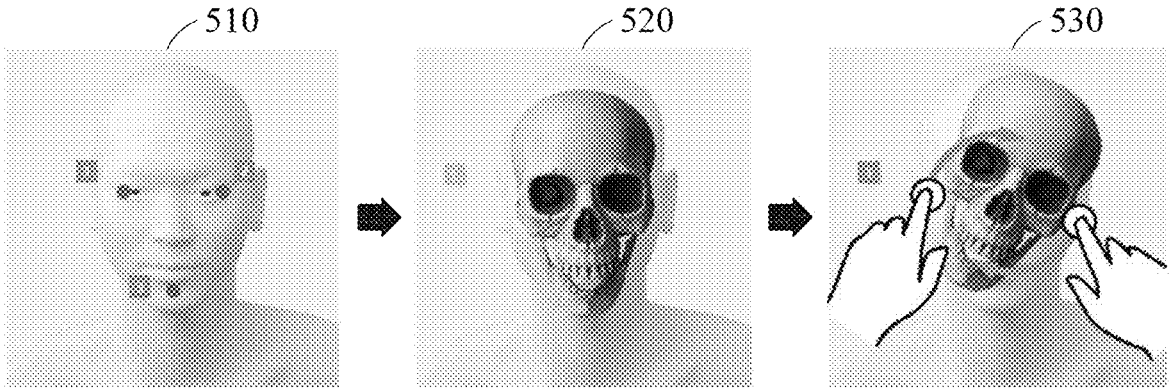

FIGS. 5A and 5B are diagrams illustrating a method of projecting a 3D image model onto a surgery subject according to another example embodiment.

FIG. 5A is a flowchart illustrating a method of projecting the 3D image model onto the surgery subject according to another example embodiment and FIG. 5B is a flowchart obtained by visualizing the flowchart of FIG. 5A.

Referring to FIGS. 5A and 5B, in user operation 510, the surgical guide device may designate three points by a user input. For example, the user may select points corresponding to two eyes and the tip of the chin based on a real-world image provided through the wearable device. When the user selects the two eyes and the tip of the chin as a gesture, the surgical guide device may recognize the user's gesture as a user input and determine the three points. The user may select the left eye as a first point, the right eye as a second point, and the tip of the chin as a third point.

In operation 520, the surgical guide device may determine the expression attribute information of the 3D image model based on the points selected by the user, and display the 3D image model on the surgery subject based on the expression attribute information. The surgical guide device may determine expression attribute information of the 3D image model to match reference points predefined in the 3D image model with the points selected by a user input.

The surgical guide device may recognize the user's gesture for adjusting the expression attribute information of the 3D image model. In operation 530, when the surgical guide device recognizes the user's gesture for adjusting the expression attribute information of the 3D image model, the surgical guide device may adjust the expression attribute information of the 3D image model based on the gesture. The user may adjust the rotation angle of the 3D image model displayed on the surgery subject as desired by the user, based on the expression attribute information of the 3D image model determined by the surgical guide device through the gesture.

Figure 6:
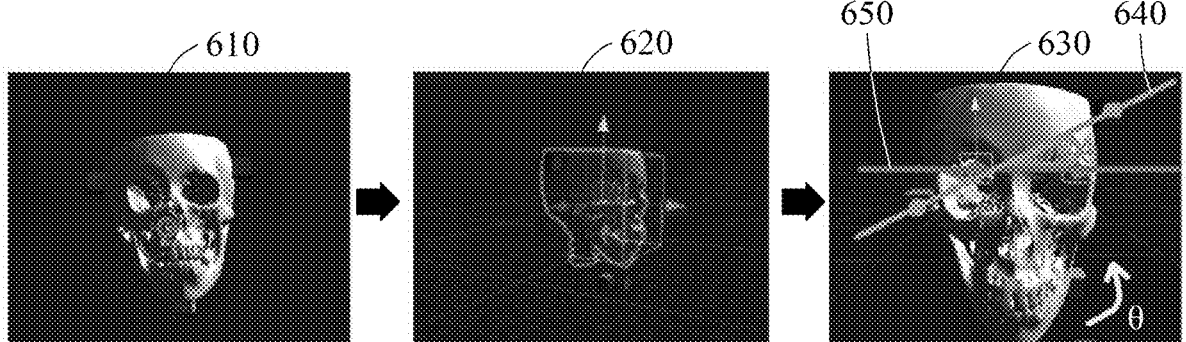
FIG. 6 is a diagram illustrating a process of mapping a 3D image model to a surgery subject according to another example embodiment.

FIG. 6 is a diagram illustrating a process of mapping a 3D image model to a surgery subject according to another example embodiment.

Referring to FIG. 6, in operation 610, the surgical guide device may determine three points selected by a user input. The surgical guide device may designate a horizontal plane based on the three points and determine a normal vector based on the horizontal plane.

In operation 620, the surgical guide device may display a 3D image model to face in a direction perpendicular to the horizontal plane including the three points using the normal vector of the horizontal plane.

It may be assumed that predefined reference points are set in the 3D image model. In operation 630, the surgical guide device may calculate an angle between a straight line 650 between reference points corresponding to the two eyes among the reference points, and a straight line 640 between points corresponding to the two eyes among the selected points. The surgical guide device may rotate the 3D image model by the calculated angle such that the straight line 650 between the reference points corresponding to the two eyes among the reference points matches to the straight line 640 between the points corresponding to the two eyes among the selected points. The surgical guide device may rotate the 3D image model by the calculated angle to map the 3D image model to the surgery subject.

Figure 7:
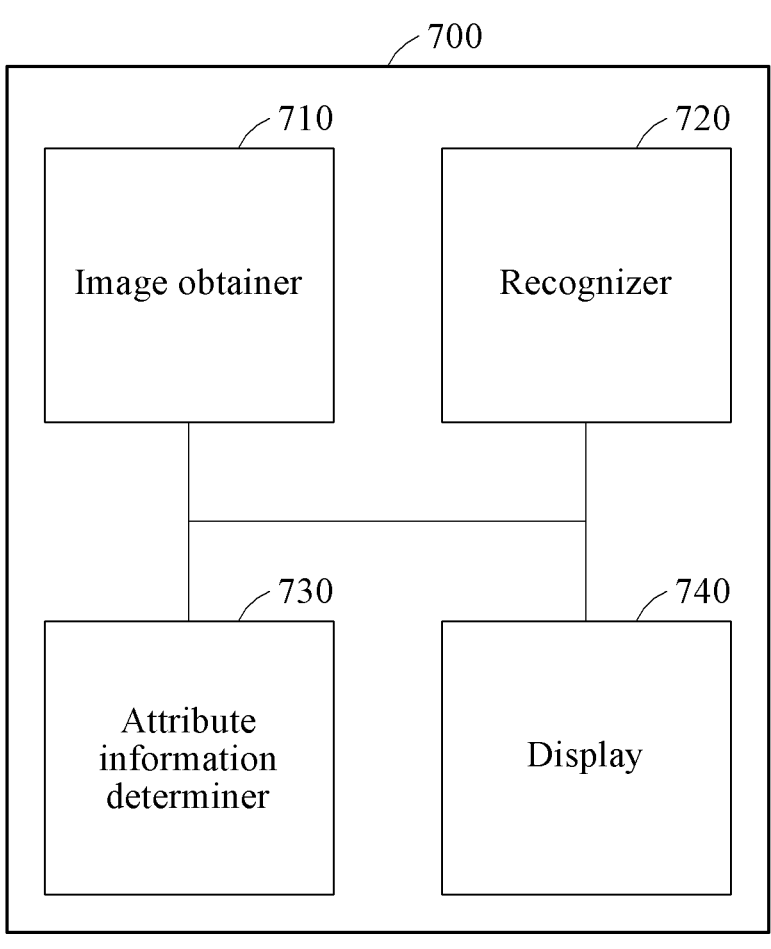
FIG. 7 is a diagram illustrating a configuration of a surgical guide device using AR according to an example embodiment.

FIG. 7 is a diagram illustrating a configuration of a surgical guide device using AR according to an example embodiment.

Referring to FIG. 7, a surgical guide device 700 may include an image obtainer 710, a recognizer 720, an attribute information determiner 730, and a display 740. In an example embodiment, the surgical guide device 700 may include one or more processors, and the one or more processors may perform operations of the recognizer 720 and the attribute information determiner 730. The surgical guide device 700 may be a surgical guide device described herein or may be an AR wearable device such as Microsoft's HoloLens.

According to an example embodiment, the image obtainer 710 may obtain an image showing a surgery subject by using a camera of a wearable device worn by the user. The image obtainer 710 may obtain an image having the same field of view and time point as those of the user.

The recognizer 720 may recognize a marker predefined in the image. The recognizer 720 may recognize at least one of position information of the marker, size information of the marker, or shape information of the marker based on the image. Also, the recognizer 720 may recognize a user's gesture for determining expression attribute information of the 3D image model.

The attribute information determiner 730 may determine expression attribute information of the 3D image model to be projected onto the surgery target based on the recognized marker. The attribute information determiner 730 may determine at least one of position information, shape information, or rotation information of the recognized marker based on the predefined marker, and determine the expression attribute information of the 3D image model to be projected onto the surgery subject based on at least one of the determined position information, shape information, or rotation information. The attribute information determiner 730 may determine at least one of direction information, size information, or position information of the 3D image model to be projected onto the surgery subject. When the recognizer 720 detects an input of a user's gesture, the attribute information determiner 730 may determine the expression attribute information of the 3D image model based on the gesture.

According to an example embodiment, the attribute information determiner 730 may collect a medical image corresponding to the surgery subject and convert the medical image into a 3D image model. The attribute information determiner 730 may convert an extension of a medical image including at least one of a CT image, an MRI image, or a 3D scan image, and perform 3D modeling.

The display 740 may display the 3D image model through the wearable device by projecting the 3D image model onto the surgery subject, based on the determined expression attribute information.

In another example embodiment, the image obtainer 710 may obtain an image showing a surgery subject by using a camera of a wearable device worn by the user. The recognizer 720 may receive a user input including points selected based on the image. In addition, the recognizer 720 may recognize a user's gesture for determining expression attribute information of the 3D image model.

The attribute information determiner 730 may calculate a target direction based on coordinate values of the selected points, and determine the expression attribute information of the 3D image model to be projected onto the surgery subject based on the target direction. The attribute information determiner 730 may determine a Z-axis direction of the 3D image model based on a straight line connecting reference points previously set in the 3D image model and a straight line connecting the selected points. When the recognizer 720 detects an input of the user's gesture, the attribute information determiner 730 may determine the expression attribute information of the 3D image model based on the gesture.

The display 740 may display the 3D image model through the wearable device by projecting the 3D image model onto the surgery subject, based on the determined expression attribute information. The display 740 may be a see-through display through which the user can see an actual surgical field. The display 740 may provide an effect such that a 3D image model is attached to a surgery subject seen through the see-through display.

The methods according to the example embodiments described herein may be recorded in non-transitory computer-readable media including program instructions to implement various operations of the example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random-access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The devices described above may be configured to act as one or more software modules in order to perform the operations of the example embodiments, or vice versa.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software may also be distributed over network coupled computer systems so that the software is stored and executed in a distributed fashion. The software and data may be stored by one or more non-transitory computer readable recording mediums.

While the example embodiments are described with reference to drawings, it will be apparent to one of ordinary skill in the art that various alterations and modifications in form and details may be made in these example embodiments without departing from the spirit and scope of the claims and their equivalents. For example, suitable results may be achieved if the described techniques are performed in a different order and/or if components in a described system, architecture, device, or circuit are combined in a different manner and/or replaced or supplemented by other components or their equivalents.

Therefore, other implementations, other example embodiments, and equivalents to the claims are also within the scope of the following claims.

The invention claimed is:

1. A surgical guide method using augmented reality (AR), the method comprising:
obtaining an image showing a surgery subject by using a camera of a wearable device worn by a user;
recognizing a marker predefined in the image;
wherein the marker is attached to a flat surface, not the surgery subject, of an operating table of the image,
determining expression attribute information of a three-dimensional (3D) image model to be projected onto the surgery subject based on the recognized marker;
when an input of a user's gesture is detected, determining the expression attribute information of the 3D image model based on the gesture; and
displaying the 3D image model through the wearable device by projecting the 3D image model onto the surgery subject, based on the determined expression attribute information,
based on a position where the marker is attached to the operating table, the surgery subject is positioned at a predetermined position,
wherein the recognizing of the marker comprises:
recognizing position information of the marker attached to the operating table, size information of the marker, and shape information of the marker,
wherein the determining of the expression attribute information of the 3D image model comprises:
tracking a space in which the surgery subject is positioned, based on the position information, the shape information, and rotation information of the recognized marker,
based on the result of the tracking the space, determining a position, a size, and a rotation angle of the surgery subject of the image; and
determining the expression attribute information of the 3D image model to be projected onto the surgery subject based on the determined the position, the size, and the rotation angle of the surgery subject.

2. The method of claim 1, wherein the determining of the expression attribute information of the 3D image model comprises:

determining at least one of direction information, size information, or position information of the 3D image model to be projected onto the surgery subject.

3. The method of claim 1, wherein a medical image corresponding to the surgery subject converted based on a horizontal plane and the 3D image model is generated based on the converted medical image.

4. A non-transitory computer-readable storage medium storing instructions that, when executed by a processor, cause the processor to perform the method of claim 1.

5. A surgical guide method using augmented reality (AR), the method comprising:

obtaining an image showing a surgery subject by using a camera of a wearable device worn by a user;

receiving a user input comprising points selected based on the image;

calculating a target direction based on coordinate values of the selected points;

determining expression attribute information of a three-dimensional (3D) image model to be projected onto the surgery subject based on the target direction;

when an input of a user's gesture is detected, determining the expression attribute information of the 3D image model based on the gesture; and displaying the 3D image model through the wearable device by projecting the 3D image model onto the surgery subject, based on the determined expression attribute information, wherein the receiving the user input comprising:

displaying the image through the wearable device; and receiving the user's gesture about selecting two eyes and the tip of the chin of the surgery subject based on the displayed image, as the user input;

wherein the displaying the 3D image model comprising:

calculating an angle between a first straight line between reference points corresponding to the two eyes among the reference points, and a second straight line between points corresponding to the two eyes among the selected points; and mapping the 3D image model to the surgery subject by rotating the 3D image model by the calculated angle such that the straight line between the reference points corresponding to the two eyes among the reference points matches to the straight line between the points corresponding to the two eyes among the selected points.

6. The method of claim 5, wherein the target direction is a direction perpendicular to a horizontal plane comprising the selected points.

7. The method of claim 5, wherein the determining of the expression attribute information of the 3D image information comprises:

determining a Z-axis direction of the 3D image model based on a straight line connecting reference points previously set in the 3D image model and a straight line connecting the selected points.

8. The method of claim 5, wherein a medical image corresponding to the surgery subject is converted based on a horizontal plane and the 3D image model is generated based on the converted medical image.

9. A non-transitory computer-readable storage medium storing instructions that, when executed by a processor, cause the processor to perform the method of claim 5.

10. A surgical guide device for performing a surgical guide method using augmented reality (AR), the surgical guide device comprising:

a processor configured to recognize a marker predefined in an image showing a surgery subject by using a camera of a wearable device worn by a user, wherein the marker is attached to a flat surface, not the surgery subject, of an operating table of the image, based on a position where the marker is attached to the operating table, the surgery subject is positioned at a predetermined position, recognize position information of the marker attached to the operating table, size information of the marker, and shape information of the marker, and configured to determine expression attribute information of a three-dimensional (3D) image model to be projected onto the surgery subject based on the recognized marker, when an input of a user's gesture is detected, determined the expression attribute information of the 3D image model based on the gesture, track a space in which the surgery subject is positioned, based on the position information, the shape information, and rotation information of the recognized marker, based on the result of the tracking the space, determine a position, a size, and a rotation angle of the surgery subject of the image; and determine the expression attribute information of the 3D image model to be projected onto the surgery subject based on the determined the position, the size, and the rotation angle of the surgery subject, a display configured to display the 3D image model through the wearable device by projecting the 3D image model onto the surgery subject, based on the determined expression attribute information.

11. The surgical guide device of claim 10, wherein the processor is configured to determine at least one of direction information, size information, or position information of the 3D image model to be projected onto the surgery subject.

12. The surgical guide device of claim 10, wherein a medical image corresponding to the surgery subject is converted based on a horizontal plane and the 3D image model is generated based on the converted medical image.

13. The surgical guide device of claim 10, wherein the processor is configured to receive a user input comprising points selected based on the image, and configured to calculate a target direction based on coordinate values of the selected points, and determine the expression attribute information of the 3D image model to be projected onto the surgery subject based on the target direction, and the target direction is a direction perpendicular to a horizontal plane comprising the selected points.

* * * * *